(12) United States Patent
Shudo

(10) Patent No.: US 8,475,836 B2
(45) Date of Patent: *Jul. 2, 2013

(54) TOPICAL PATCH FOR PAIN RELIEF USING COOLING AGENT

(75) Inventor: Jutaro Shudo, San Jose, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/312,744

(22) Filed: Dec. 6, 2011

(65) Prior Publication Data

US 2012/0076850 A1   Mar. 29, 2012

Related U.S. Application Data

(63) Continuation of application No. 11/305,307, filed on Dec. 16, 2005, now Pat. No. 8,105,624.

(60) Provisional application No. 60/641,482, filed on Jan. 4, 2005.

(51) Int. Cl.
*A61F 13/02* (2006.01)
*A61F 13/00* (2006.01)
*A61L 15/16* (2006.01)
*A61K 9/70* (2006.01)

(52) U.S. Cl.
USPC ............................ 424/448; 424/449; 424/443

(58) Field of Classification Search
None
See application file for complete search history.

(56) References Cited

U.S. PATENT DOCUMENTS

| | | | |
|---|---|---|---|
| 4,020,153 | A | 4/1977 | Rowsell et al. |
| 4,032,661 | A | 6/1977 | Rowsell et al. |
| 4,033,994 | A | 7/1977 | Watson et al. |
| 4,034,109 | A | 7/1977 | Rowsell et al. |
| 4,059,118 | A | 11/1977 | Watson et al. |
| 4,060,091 | A | 11/1977 | Watson et al. |
| 4,070,449 | A | 1/1978 | Rowsell et al. |
| 4,070,496 | A | 1/1978 | Rowsell et al. |
| 4,150,052 | A | 4/1979 | Watson et al. |

(Continued)

FOREIGN PATENT DOCUMENTS

| | | |
|---|---|---|
| EP | 1454623 | 9/2004 |
| EP | 1495738 | 1/2005 |

(Continued)

OTHER PUBLICATIONS

Airaksinen, et al., "Efficacy of cold gel for soft tissue injuries: a prospective randomized double-blinded trial", AM J Sports Med, 2003, 31:680-4.

(Continued)

*Primary Examiner* — Isis Ghali
(74) *Attorney, Agent, or Firm* — Rudy J. Ng; Bret E. Field; Bozicevic, Field & Francis, LLP

(57) ABSTRACT

Topical patch preparations that contain an odorless physiological cooling agent, and methods for using the same are provided. The subject topical patch preparations are made up of an adhesive gel composition that is present on a support, where the adhesive gel composition includes the odorless physiological cooling agent, a water-soluble polymer gel, water and a water holding agent. In using the subject topical patch preparations, the topical patch preparations are applied to a skin surface of a subject and maintained at the site of application for a period of time sufficient for an effective amount of the an odorless physiological cooling agent to be administered to the subject. The subject invention finds use in a variety of applications.

11 Claims, 1 Drawing Sheet

U.S. PATENT DOCUMENTS

| | | | |
|---|---|---|---|
| 4,153,679 A | 5/1979 | Rowsell et al. |
| 4,172,887 A | 10/1979 | Vanlergerghe et al. |
| 4,193,936 A | 3/1980 | Watson et al. |
| 4,226,988 A | 10/1980 | Watson et al. |
| 4,230,688 A | 10/1980 | Rowsell et al. |
| 4,296,093 A | 10/1981 | Rowsell et al. |
| 4,296,255 A | 10/1981 | Roswell et al. |
| 4,459,425 A | 7/1984 | Amano et al. |
| 5,266,592 A | 11/1993 | Grub et al. |
| 5,407,665 A | 4/1995 | McLaughlin et al. |
| 5,608,119 A | 3/1997 | Amano et al. |
| 5,622,992 A | 4/1997 | Beck |
| 5,760,085 A | 6/1998 | Beck et al. |
| 5,773,410 A | 6/1998 | Yamamoto |
| 5,780,047 A | 7/1998 | Kamiya et al. |
| 5,891,920 A | 4/1999 | Hirano et al. |
| 5,959,161 A | 9/1999 | Kenmochi et al. |
| 6,120,803 A | 9/2000 | Wong et al. |
| 6,143,353 A | 11/2000 | Oshlack et al. |
| 6,183,766 B1 | 2/2001 | Sine et al. |
| 6,214,788 B1 | 4/2001 | Velazco et al. |
| 6,244,265 B1 | 6/2001 | Cronk et al. |
| 6,267,974 B1 | 7/2001 | Suares et al. |
| 6,277,385 B1 | 8/2001 | Luke |
| 6,328,982 B1 | 12/2001 | Shiroyama et al. |
| 6,359,168 B1 | 3/2002 | Frerot et al. |
| 6,455,080 B1 | 9/2002 | Wolf et al. |
| 6,497,859 B1 | 12/2002 | Zanone et al. |
| 6,514,484 B2 | 2/2003 | Rajaiah et al. |
| 6,592,884 B2 | 7/2003 | Hofmann et al. |
| 6,649,178 B2 | 11/2003 | Mohammadi et al. |
| 6,656,456 B2 | 12/2003 | Dodd et al. |
| 6,677,391 B1 | 1/2004 | Rajaiah et al. |
| 6,719,995 B2 | 4/2004 | Rajaiah et al. |
| 6,740,311 B2 | 5/2004 | White, Jr. et al. |
| 6,769,428 B2 | 8/2004 | Cronk et al. |
| 6,821,507 B2 | 11/2004 | Glandorf et al. |
| 7,013,889 B2 | 3/2006 | Cronk et al. |
| 7,482,378 B2 | 1/2009 | Erman et al. |
| 2002/0013304 A1 | 1/2002 | Wilson et al. |
| 2002/0143047 A1 | 10/2002 | Galer et al. |
| 2002/0176886 A1 | 11/2002 | Shudo et al. |
| 2003/0091620 A1 | 5/2003 | Fikstad et al. |
| 2003/0175328 A1 | 9/2003 | Shefer et al. |
| 2004/0067970 A1 | 4/2004 | Foster et al. |
| 2005/0129744 A1 | 6/2005 | Caldwell et al. |
| 2006/0159734 A1 | 7/2006 | Shudo |
| 2007/0185237 A1 | 8/2007 | Rajaiah et al. |
| 2007/0259354 A1 | 11/2007 | Servant et al. |

FOREIGN PATENT DOCUMENTS

| | | |
|---|---|---|
| GB | 2302651 | 1/1997 |
| JP | 2004-59474 | 2/2004 |
| WO | WO 0045815 | 8/2000 |
| WO | WO 0051586 | 9/2000 |
| WO | WO 02072081 | 2/2002 |
| WO | WO 2006073767 | 7/2006 |

OTHER PUBLICATIONS

Behrendt, H.J. et al., "Characterization of the mouse cold-menthol receptor TRPM8 and vanilloid receptor type-1 VR1 using a flourometric imaging plate reader (FLIPR) assay", British Journal of Pharmacology, 2004, 141:737-45.

Benoliel, et al., "Paroxysmal hemicrania. Case studies and review of the literature", Oral Surg Oral Med Oral Pathol Oral Radiol Endod, 1998, 85:285-92.

Bhargav, et al., "Shoulder stiffness: diagnosis", Aust Fam Physician, 2004 33:143-7.

Davies, et al., "A novel treatment of postherpetic neuralgia using peppermint oil", Clin J Pain, 2002, 18:200-2.

Gennaro, "Remington: the science and practice of pharmacy", 20th Edition, 2000, 836, 845-9, 854-6, 966-7.

Pascarelli, et al., "Understanding work-related upper extremity disorders: clinical findings in 485 computer users, musicians, and others", J Occup Rehabil, 2001, 11:1-21.

Peier, et al., "A TRP channel that senses cold stimuli and menthol", Cell, 2002, 108:705-15.

Turner, et al., "Prediction of chronic disability in work-related musculoskeletal disorders: a prospective, population-based study", BMC Musculoskelet Disord, 2004, 5:14.

TOPICAL PATCH FOR PAIN RELIEF USING COOLING AGENT

CROSS-REFERENCE TO RELATED APPLICATIONS

Pursuant to 35 U.S.C. §119 (e), this application claims priority to the filing date of the U.S. Provisional Patent Application Ser. No. 60/641,482 filed Jan. 4, 2005, the disclosure of which is herein incorporated by reference.

INTRODUCTION

Background of the Invention

Tissue inflammation is the result of interconnected physiological events. Inflammation of the skin, which is associated with tissue damage, can result from various skin disorders such as eczema, psoriasis, seborrheic dermatitis, contact dermatitis, allergic dermatitis, etc. Inflammation is also associated with tissue damage resulting from ultraviolet or thermal burns, attack by certain micro-organisms, insect bites, stings, etc. Inflammation of deeper structures, the muscles, tendons, bursa, and joints, which is associated with tissue damage, can result from physical trauma, e.g. sprains, strains, contusions, strenuous exercise, etc. Such inflammation may result in bursitis, tendinitis, and muscle soreness. Inflammation is also associated with tissue damage resulting from metabolic disorders, such as gout, or from immunologic disorders, such as rheumatoid arthritis, or from changes associated with aging, such as osteoarthritis.

Symptoms of inflammation are erythema (redness), edema (swelling), heat, pain, and loss of function. The immediate consequence of tissue damage is the release of certain chemical agents which are mediators of inflammation, i.e., these materials evoke and intensify the events which result in the redness, swelling, pain and heat. Examples of these chemical agents are histamine, seratonin and the kinins.

Today, various topical patch formulations are employed to relieve pains such a stiff shoulder, back pain, inflammation, and so on. General active ingredients of these topical patch preparations are menthol, camphor and mint oil as a cooling effect counterirritant. However, a problem with these cooling agents is their strong odor, which can be found offensive.

Accordingly, there is a continued interest therefore in the development of new topical cooling agent compositions that could efficiently treat a subject suffering from the above conditions.

RELEVANT LITERATURE

U.S. Pat. Nos. 4,296,255; 4,296,093; 4,230,688; 4,226,988; 4,193,936; 4,153,679; 4,150,052; 4,070,496; 4,070,449; 4,060,091; 4,059,118; 4,034,109; 4,033,994; 4,032,661; 4,020,153; 5,266,592; 4,459,425; 5,773,410; 6,267,974; 6,592,884; 5,959,161; 6,328,982; 6,359,168; 6,214,788; 5,608,119; 6,769,428; 6,455,080; 6,656,456; 6,821,507; 6,740,311, 6,677,391; 6,497,859; 6,769,428 and 6,719,995; Japanese Patent No. 2004059474; United States Patent Application No. 20040067970.

SUMMARY OF THE INVENTION

Topical patch preparations that contain an odorless physiological cooling agent, and methods for using the same are provided. The subject topical patch preparations are made up of an adhesive gel composition that is present on a support, where the adhesive gel composition includes the odorless physiological cooling agent, a water-soluble polymer gel, water and a water holding agent. In using the subject topical patch preparations, the topical patch preparations are applied to a skin surface of a subject and maintained at the site of application for a period of time sufficient for an effective amount of the an odorless physiological cooling agent to be administered to the subject. The subject invention finds use in a variety of applications.

DETAILED DESCRIPTION

Figure 1:
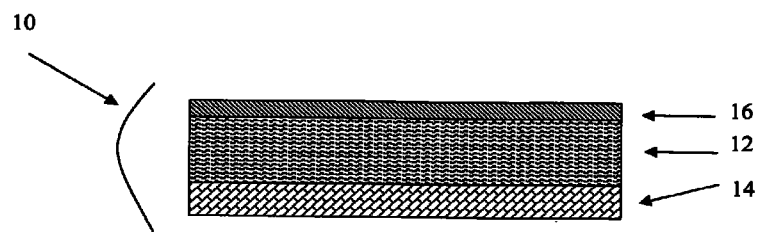
FIG. 1 provides a cross-sectional view of a topical patch preparation according to an embodiment of the invention.

Topical patch preparations that contain an odorless physiological cooling agent, and methods for using the same are provided. The subject topical patch preparations are made up of an adhesive gel composition that is present on a support, where the adhesive gel composition includes the odorless physiological cooling agent, a water-soluble polymer gel, water and a water holding agent. In using the subject topical patch preparations, the topical patch preparations are applied to a skin surface of a subject and maintained at the site of application for a period of time sufficient for an effective amount of the an odorless physiological cooling agent to be administered to the subject. The subject invention finds use in a variety of applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Topical Patch Preparations

As summarized above, the subject invention is directed to topical patch preparations of an odorless physiological cooling agent. The topical patch preparations of the subject invention are characterized by having an effective amount of the odorless physiological cooling agent present in a gel adhesive base. FIG. 1 provides a representation of a topical patch preparation described according to the subject invention. As can be seen in FIG. 1, this representative topical patch preparation 10 contains a gel adhesive base 12 present on a support 14. Each of these components is now described in greater detail.

The gel adhesive base which serves as the retaining layer, is made up of the odorless physiological cooling agent that is present in, e.g., dissolved in or dispersed in, and adhesive gel base. By "physiological cooling agent" is meant an agent that, when contacted with skin of a subject, imparts a cooling sensation or effect to the subject, in a manner analogous to the cooling effect of menthol. By "odorless" is meant that the odor of the agent is less pungent than the odor of menthol.

| Chemical Name | Description |
| --- | --- |
| Menthol | Natural compound, Strong odor |
| WS-3 | As an almost odorless |
| WS-23 | As an almost odorless |
| Frescolat ML | Faintly minty in oder |

WS-3: (N-Ethyl-p-menthane-3-carboxamide), supplyed by Millennium Chemical
WS-23: (2-Isopropyl-N,2,3-trimethylbutyramide), supplyed by Millennium Chemical
Frescolat ML: (−)-Menthyl lactate, supplyed by Haarmann & Reimer)

In certain embodiments, the cooling agent is an acyclic amide, where representative acyclic amids include compounds of the formula:

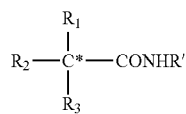

where $R_1$, $R_2$ and $R_3$ are each $C_1$-$C_5$ alkyl and together provide a total of at least 3, such as from about 3-10, including from about 5-10, carbon atoms; and R' is $C_1$-$C_5$ alkyl, $C_1$-$C_8$ hydroxyalkyl or alkylcarboxyalkyl of up to 8 carbon atoms. In this group $R_1$ is in representative embodiments, methyl, ethyl or n-propyl and one or both of $R_2$ and $R_3$ is branched in an alpha or beta position relative to the carbon atom marked (*). In representative embodiments, the cooling agent is N,2,3-trimethyl-w-isopropylbutamide (also known as WS-23; trimethyl isopropyl butanimide, CAS#51115-67-4).

The above compounds can be produced using any convenient protocol, where representative protocols are described in U.S. Pat. No. 4,296,255.

Other representative odorless physiological cooling agents of interest include, but are not limited to: linalool, geraniol, hydroxycitronellal, WS-3 (Millennium Chemical), Flescolat-MGA (Haarman & Reimer), FrescolatML (Haarmann & Reimer), PMD38 (Takasago), CoolactP (Takasago) and Cooling Agent 10 (Takasago); and the like.

The amount of odorless physiological cooling agent that is present in the adhesive gel base is an amount sufficient to administer to a subject an effective amount of the agent when applied to a skin surface of the subject, as described in greater detail below. In many embodiments, the amount of odorless physiological cooling agent present in the adhesive gel base ranges from about 0.1 to 15.0% (w/w), sometimes from about 0.5 to 10.0% (w/w), such as from about 1.0 to 8.0% (w/w) and including from about 2.0 to 7.0% (w/w).

The adhesive gel base that includes the agent, as described above, is made up of a water-soluble high molecular weight substance, water and a water-retaining agent. In certain embodiments, the adhesive gel base may further include a cosolvent, e.g., an organic cosolvent. Each of these components is now described separately in greater detail.

Water-soluble high molecular weight substances of interest include water-soluble polymers, where polymers of interest include, but are not limited to: gelatin, starch, agar, mannan, alginic acid, polyacrylic acid, sodium polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, and starch acrylate copolymer or other starch sodium acrylate graft copolymers. Metallic salts of these, as well as the products of cross-linking these by means of organic or inorganic cross-linking agents, are also of interest. These water-soluble polymers can be used to bring out the properties and characteristics of the other starting materials used in the adhesive gel composition, and in practice can be used alone or in combinations of 2 or more. The amount of water soluble high molecular weight substance(s) present in the adhesive gel base generally ranges from about 0.5 to 20, such as from a bout 2 to 20% (w/w).

While any convenient water may be employed as the water component, of interest are distilled water or ion-exchange water or the like, which is preferred in many embodiments of the subject invention. The amount of water present in the gel adhesive is sufficient to impart the desired physical properties to the gel adhesive, and to improve the swelling of the horny or keratinized layer of the skin to thereby improve the permeability or penetration of active agent(s), where the amount of water in the gel composition generally ranges from about 10 to 80%, such as from about 30 to 60% (w/w).

The water-retaining agent or water-holding agent of the subject adhesive gel compositions is any agent that is capable of at least diminishing the volatilization of water contained in the adhesive gel base so that the water content in the adhesive gel base is maintained at least a substantially constant, if not constant, level during storage and use of the preparation. One or more water-retaining agents may be employed in the subject compositions, where the amount of water-retaining agent present in the adhesive gel base may range from about 1 to 70%, such as from about 10 to 60% by weight. Examples of suitable water-retaining or water-holding agents include, but are not limited to: 1 or more types of polyvalent or polyhydric or sugars or alcohols, such as glycerin, sorbitol, propylene glycol, diethylene glycol, 1,3-butylene glycol, and ethylene glycol, and the like.

In addition, the subject gel base compositions may also include a cosolvent, where the cosolvent is generally an organic cosolvent. Examples of cosolvents of interest include, but are not limited to: n-methyl-2-pyrrolidone, deet, ethyl alcohol, methyl alcohol, polyethylene glycol (e.g., low molecular weight polyethylene glycol, such as PEG 600 or lower, e.g., 500, 400, 300, 200, 100 etc and blends) thereof, and isopropyl myristate, etc. The cosolvent may be made up of a simple component or be incombination of two or more components.

Furthermore, in addition to the aforementioned ingredients, various additives that are used in ordinary topical water-soluble patch preparations may also be suitably compounded as needed, including inorganic substances such as kaolin, bentonite, and titanium dioxide; preservatives such as paraben; anionic, cationic, and nonionic surfactants; metallic aluminum crosslinking agents such as aluminum chloride, dried aluminum hydroxide gel, and dihydroxyaluminum aminoacetate; oils such as jojoba oil and castor oil; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents.

The pH of the gel base composition typically is one that lies in a physiologically acceptable range, where the pH typically may range from about 4.0 to 7.0, such as from about 4.0 to 6.0.

As mentioned above, the adhesive gel composition containing the one or more active ingredients is typically present on a support or backing. The support is generally made of a flexible material which is capable of fitting in the movement of human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like.

In addition to the adhesive gel composition and the support layer, the subject topical patches may also include a release film 16 on the surface of the gel layer opposite the backing that provides for protection of the gel layer from the environment. The release film may be any convenient material, where representative release films include polyesters, such as PET or PP, and the like.

In many embodiments, the patch is present in a sealed package. Generally, the sealed package is fabricated from a packaging material that includes a layer made out of a material capable of preventing passage of moisture, oxygen and other agents, i.e., the package includes in a moisture/oxygen barrier material. Any suitable barrier material may be employed, where barrier materials of interest include metallic layers, e.g., aluminum, where in many embodiments, the barrier layer is an aluminum layer. This barrier layer has a thickness sufficient to provide for the barrier function, where the thickness typically ranges from about 5 to 15, usually from about 6 to 10 μm. In many embodiments, the package is a laminate of the barrier layer in combination with one or more additional layers, e.g., polymeric layers, paper layers, etc. A representative aluminum containing package that may be used with the subject patch preparations is sold by Dainippon Printing Co., Ltd. (Kyoto, Japan).

The topical patch preparations may be fabricated using any convenient protocol. One convenient protocol for fabrication of the subject patches includes preparing a gel adhesive paste through the uniform mixing of the aforementioned ingredients and then coating the paste onto the support, followed by cutting of the resultant product to the specified size to obtain the desired topical patch preparation. The resultant topical patch preparation is then heat-sealed, typically several sheets to a package, using a packaging material containing an aluminum layer, as described supra, to obtain the sealed topical patch. For a more detailed description of the fabrication protocol, see U.S. Pat. No. 5,827,529; the disclosure of which is herein incorporated by reference.

Figure 2:
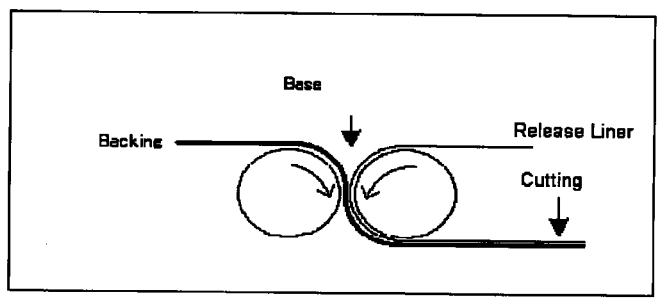
FIGS. 2 and 3 provide schematic representations of the manufacturing process for topical patch preparations according to an embodiment of the invention.

In a representative fabrication protocol, the base used in the present invention is produced by using a mixer to uniformly blend the aforementioned ingredients by means of any convenient protocol into a paste, which is then spread by means of a spreader onto a backing or support material. As indicated above, the support material may be, for example, paper, or a woven or nonwoven cloth made of PET or PP or some other polyester fiber. For protection, the surface thereof is then covered with a release film of a polyester such as PET or PP. These steps are illustrated in FIG. 2.

As is described in greater detail below, in representative embodiments the hydrogel patch compositions are self-adhesive, i.e., inherently adhesive, and thus may be fixed in a position over the skin wound, i.e., removably bonded to and/or about a given skin wound, without the use of additional adhesives or other means to hold the patch in place over the formulation. For example, the hydrogel composition matrix may itself be adhesive.

In representative embodiments, the hydrogel compositions are adhesive, as determined using the Japanese Industrial Standards (JIS) Z-0237 adhesive strength measurement protocol (see e.g., U.S. Application Ser. No. 60/615,320 titled "METHODS AND COMPOSITIONS FOR TREATING SKIN WOUNDS and filed on Dec. 1, 2004; the disclosure of which is herein incorporated by reference). A given hydrogel composition is considered to be adhesive if it stops at least a No. 3 size ball, such as at least about a No. 4 size ball, including at least a bout a No. 5 size ball, in this protocol. In certain embodiments, the composition is sufficiently adhesive to stop a No. 6 ball or greater, e.g., No. 7 ball or greater, e.g., No. 8 ball or greater, e.g., No. 9 ball or greater. In certain embodiments, the subject compositions are differentially adhesive, in that they show greater adhesiveness to non-living, as opposed to living matter.

In certain other embodiments a subject hydrogel patch composition may be held in a fixed position about a skin wound using a separate adhesive such as an adhesive backing or the like or a combination of inherent adhesiveness and an additional separate adhesion means may be employed.

Certain hydrogel patch compositions may be adapted and employed for use with the subject invention. Representative hydrogel patch compositions that may be adapted for use with the subject invention include, but are not limited to those described in PCT International Publication Nos.: WO 02/078757 and WO 02/078756 and U.S. Pat. Nos. 5,120,544; 5,160,328; 5,270,358; 5,423,737; 5,476,443; 5,489,262; 5,501,661; 5,827,529; 6,039,940; 6,096,333; 6,214,374; 6,296,869; 6,348,212; 6,455,065; the disclosures of which are herein incorporated by reference.

Figure 3:
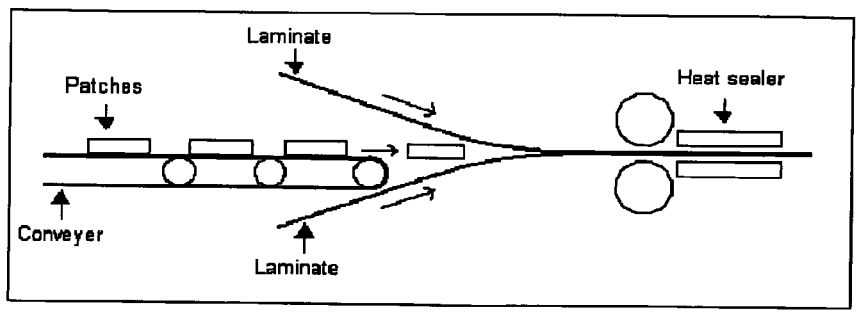

The resulting product is then cut to the specified size to obtain the desired topical patch preparation composition. The shape of the patch may vary, where representative shapes include square, rectangle, oval, circle, etc. The size of the patch may also vary, where in many embodiments the size ranges from about 1 to 200 cm$^2$, and in many embodiments from about 10 to 180 cm$^2$, usually from about 100 to 150 cm$^2$, e.g., 140 cm$^2$. The weight of the base in the final topical patch may be from about 300 to about 1500 g/m$^2$, such as from about 600 to about 1200 g/m$^2$. This water-soluble topical patch preparation is then packaged by means of a heat seal in a packaging material that includes a layer of aluminum to obtain the final product, as shown in FIG. 3.

It should be noted that the above manufacturing protocols are merely representative. Any convenient protocol that is capable of producing the subject topical patch preparations, as described above, may be employed.

Methods of Using Patch Preparations

The subject patch preparations find use in applications of topically delivering a cooling agent to a subject, particularly the skin of a subject. In practicing the invention, the patch may be administered to any convenient topical site. Topical sites of interest include, but are not limited to: arms, leg, torso, head, etc. The surface area that is covered by the topical patch preparation following application must be sufficient to provide for the desired amount of agent administration, and in many embodiments ranges from about 1 to 200 $cm^2$, and in many embodiments from about 10 to 180 $cm^2$, usually from about 100 to 150 $cm^2$, e.g., 140 $cm^2$.

In representative embodiments, the period of time required to deliver the desired amount of agent is generally not exceeding about 48 hours, usually not exceeding about 24 hours. However, the period of time during which the preparation is maintained at the application site is, in many embodiments, at least about 30 minutes, usually at least about 1 hour.

In practicing the subject methods, a topical patch may be applied a single time or a plurality of times over a given time period, e.g., the course of the disease condition being treated, where the dosing schedule when a plurality of patches are administered over a given time period may be daily, weekly, biweekly, monthly, etc.

The above described patches and methods find use in any application in which the administration of a physiological cooling agent to a subject is desired. Among other applications, the topical application the cooling agent according to the subject methods as described herein is effective for treating inflammation, aches, etc., including the maladies reviewed in the introduction section of this application. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In representative embodiments, the subject methods find use in the treatment of a disease condition. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, side effects associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. As such, treatment includes both curing and managing a disease condition.

Kits

Also provided are kits, where the subject kits at least include one or more topical patch preparations, as described above. The subject topical patch preparations in the kits may be present in a package, as described supra. The topical patches of the kits are typically present in individual pouches or analogous containers, to preserve the composition of the patches until use. The subject kits also generally include instructions for how to use the patches, where the instructions typically include information about where to apply the patch, dosing schedules etc. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

The following practical and comparative examples are offered by way of illustration and not by way of limitation.

EXAMPLES

Practical and comparative examples are given below, but the manufacturing method is not limited thereby.

I. Preparation of Topical Patches

A water-soluble polymer topical patch preparation in which WS-23 has been compounded in an amount of 5% and 7%. WS-23 is blended with the ingredients listed in Table 1 into uniformity and adjusted into a paste, which is then spread onto a PET nonwoven cloth to a weight of 1000 $g/m^2$; the resulting product is then laminated with a PP film and then cut into 10 cm×14 cm.

TABLE 1

| Chemical Name | Practical Example 01 Concentration (%) | Practical Example 02 Concentration (%) |
|---|---|---|
| Disodium Edetate | 0.07 | 0.07 |
| WS-23 | 5 | 7 |
| Castor Oil | 10 | 15 |
| Methylparaben | 0.15 | 0.15 |
| Kaolin | 2 | — |
| D-Sorbitol | 20 | 20 |
| Polyacrylic acid | 4.0 | 6.0 |
| Polyvinyl Alcohol | 1.6 | 2.0 |
| Tartaric Acid | 0.5 | 0.5 |
| Dihydroxyaluminium amino acetate | 0.05 | 0.06 |
| Sodium Polyacrylate | 3.5 | 3.5 |
| Cellulose Gum | 2.5 | 2.0 |
| Hydroxy propyl cellulose | 0.3 | 0.5 |
| Glycerin | 15 | 17 |
| Water | 35.33 | 26.22 |
| Total | 100.0% (w/w) | 100.0% (w/w) |
| PH | 4.8 | 4.5 |

* All values are expressed in terms of % (w/w).

II. Stability Data

Stability data on the WS-23 content and patch adhesive strength in the practical example 01. The experiment was conducted in an environment of 40° C. and 75% humidity. The results are shown in a comparison with the initial value, which was taken to be 100% and are provided in Table 2.

TABLE 2

| | Initial | 1 month | 2 months | 4 months | 6 months |
|---|---|---|---|---|---|
| WS-23 Concentration | 101.0% | 101.1% | 99.9% | 99.9% | 100.2% |
| Adhesive strength | No. 4 Steel ball (2.0 g) stopped | No. 4 Steel ball (2.0 g) stopped | No. 4 Steel ball (2.0 g) stopped | No. 4 Steel ball (2.0 g) stopped | No. 4 Steel ball (2.0 g) stopped |

*Adhesive strength measurement method: Japanese Industrial Standards(JIS) Z-0237

III. Activity Assay

The WS-23 topical patch preparation of the practical example 01 was applied to patient volunteers who suffer from stiff shoulder, back pain, muscle fatigue pain and carpal tunnel syndrome (CTS) to investigate its efficacy.

The WS-23 topical patch preparation of practical example 01 was applied to the affected area of 4 volunteers for 12 hours The pain level prior to application and 30 minutes post application was measured for each subject.

The results are shown below in Table 3.

TABLE 3

|  | Initial | Disorder | Pre | Post |
|---|---|---|---|---|
| Patient 1 | JS | Stiff shoulder | 07 | 05 |
| Patient 2 | MY | Back pain | 06 | 04 |
| Patient 3 | TA | Muscle fatigue pain | 07 | 02 |
| Patient 4 | SS | CTS | 08 | 06 |

*Pain Level:

10: Disabling, Must take care of pain.

08: Severe, Can't concentrate and can't do all but simple things.

06: Moderate, But able to continue some physical activity.

04: Tolerate, Can be ignored somewhat.

02: Mild, Aware of undercurrent of mild pain.

00: Pain Free

It is evident from the above results and discussion that the subject invention provides an important new cooling sensation counterirritant topical patch composition, which composition offers benefits over current topical formulations, including lack of odor. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A topical patch preparation comprising:
   (a) an adhesive gel composition having a pH ranging from about 4.0 to 7.0 and comprising:
      (i) a drug consisting of N,2,3-trimethyl-2-isopropylbutamide in a pain-relieving effective amount ranging from about 0.1 to 15.0% (w/w);
      (ii) a water-soluble polymer gel;
      (iii) water in an amount ranging from about 10 to 80% (w/w); and
      (iv) a water retaining agent; and
   (b) a support.

2. The topical patch preparation according to claim 1, wherein said N,2,3-trimethyl-2-isopropylbutamide is present in an amount ranging from about 0.5 to 10.0% (w/w).

3. The topical patch preparation according to claim 1, wherein said water is present in an amount ranging from about 20 to 70% (w/w).

4. The topical patch preparation according to claim 3, wherein said water is present in an amount ranging from about 30 to 60% (w/w).

5. The topical patch preparation according to claim 1, wherein said pH ranges from about 4.0 to 6.0.

6. A topical patch preparation comprising:
   (a) an adhesive gel composition having a pH ranging from about 4.0 to 6.0 and comprising:
      (i) a drug consisting of N,2,3-trimethyl-2-isopropylbutamide in a pain-relieving effective amount ranging from about 0.5 to 10.0% (w/w);
      (ii) a water-soluble polymer gel;
      (iii) water in an amount ranging from about 30 to 60% (w/w);
      (iv) a water retaining agent;
   (b) a support.

7. A method of delivering N,2,3-trimethyl-2-isopropylbutamide to a subject, said method comprising:
   (a) applying a topical patch preparation comprising:
      (i) an adhesive gel composition comprising a drug consisting of a pain-relieving effective amount of N,2,3-trimethyl-2-isopropylbutamide; and
      (ii) a support;
   to a skin surface of said subject; and
   (b) maintaining said topical patch preparation on said skin surface for a period of time sufficient for said N,2,3-trimethyl-2-isopropylbutamide to be delivered to said subject.

8. A kit comprising:
   (a) a topical patch preparation comprising:
      (i) an adhesive gel composition comprising a drug consisting of a pain-relieving effective amount of N,2,3-trimethyl-2-isopropylbutamide; and
      (ii) a support; and
   (b) instructions for using said preparation.

9. The kit according to claim 8, wherein said kit comprises a plurality of said topical patch preparations.

10. The kit according to claim 9, wherein said plurality of topical patch preparations are present in separate containers.

11. The kit according to claim 10, wherein said separate containers are sealed pouches.

* * * * *